(12) United States Patent
Davidsen et al.

(10) Patent No.: US 12,389,171 B2
(45) Date of Patent: Aug. 12, 2025

(54) HEARING AID COMPRISING AT LEAST ONE EEG SIGNAL PROCESSING CIRCUIT

(71) Applicant: Oticon A/S, Smoerum (DK)

(72) Inventors: Jeppe Gaardsted Davidsen, Smoerum (DK); Niels Marker-Villumsen, Smoerum (DK)

(73) Assignee: Oticon A/S, Smçrum (DK)

( * ) Notice: Subject to any disclaimer, the term of this patent is extended or adjusted under 35 U.S.C. 154(b) by 219 days.

(21) Appl. No.: 18/187,719

(22) Filed: Mar. 22, 2023

(65) Prior Publication Data

US 2023/0319490 A1    Oct. 5, 2023

(30) Foreign Application Priority Data

Mar. 31, 2022   (EP) ..................................... 22165922

(51) Int. Cl.
 *H04R 25/00*   (2006.01)
(52) U.S. Cl.
 CPC ......... *H04R 25/505* (2013.01); *H04R 25/603* (2019.05); *H04R 2225/33* (2013.01); *H04R 2225/81* (2013.01)

(58) Field of Classification Search
 CPC ............... H04R 25/505; H04R 25/603; H04R 2225/33; H04R 2225/81; H04R 25/609; H04R 25/50; H04R 2225/43; A61B 5/304; A61B 5/31
 See application file for complete search history.

(56) References Cited

U.S. PATENT DOCUMENTS

2014/0171775 A1   6/2014   Kilsgaard et al.
2017/0281037 A1   10/2017  Kidmose et al.

FOREIGN PATENT DOCUMENTS

EP    4059429    3/2022

OTHER PUBLICATIONS

Kangping Hu, "Low Noise CMOS ISFETs Using In-Pixel Chopping", 2019 IEEE Biomedical Circuits and Systems Conference (BIOCAS), IEEE, Oct. 17, 2019 (Oct. 17, 2019), pp. 1-4.

*Primary Examiner* — Tuan D Nguyen

(57) ABSTRACT

The present disclosure relates to a hearing aid comprising at least one sensor configured to provide a sensing signal, and at least one sensing signal processing circuit, comprising a first switch bias buffer circuit comprising a first voltage buffer configured to receive the sensing signal and to provide a first buffer signal at a reduced impedance node, and a first switching circuit configured to modulate the output voltage of the first voltage buffer.

12 Claims, 11 Drawing Sheets

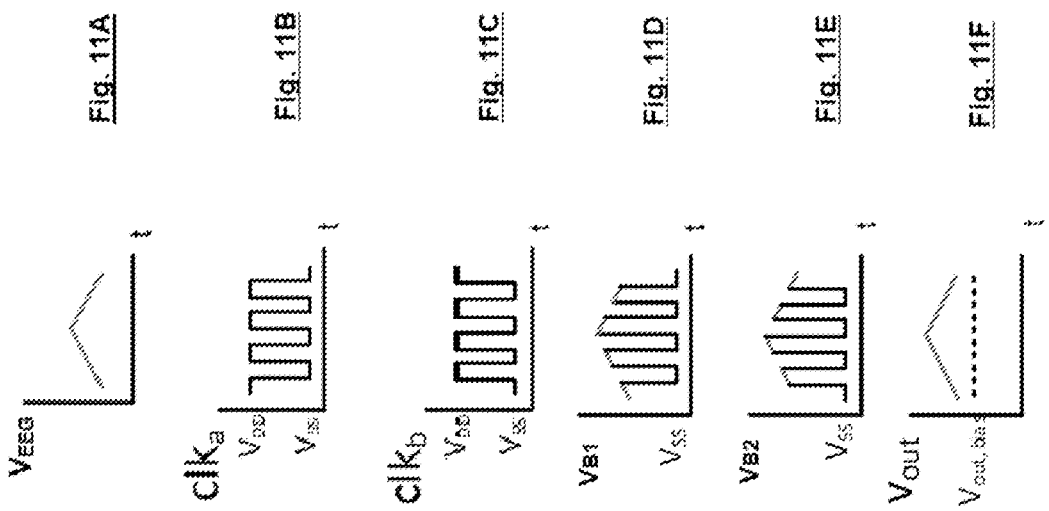

HEARING AID COMPRISING AT LEAST ONE EEG SIGNAL PROCESSING CIRCUIT

FIELD

The present disclosure relates to a hearing aid comprising at least one sensor configured to provide a sensing signal, such as an electrode configured to provide a bio response signal of a user of the hearing aid, e.g. an Electroencephalography (EEG) signal, the hearing aid further comprising at least one capacitive sensing signal processing circuit, such as a bio response signal processing circuit.

BACKGROUND

EEG signals are electrical signals representing a person's brain electrical activity.

An EEG signal can be measured by an electrode such as a small capacitive electrode located in a hearing aid. It is then possible to use the EEG signal to control or adjust signal processing in the hearing aid.

However, because EEG signals are low frequency signals, the measure of these EEG signals by small capacitive electrode requires, at the level of the electrode, a high input impedance, which is typically higher than 150 Giga Ohms. Specifically, as shown in FIG. 1, by increasing the input impedance R1, R2, it is possible to obtain a better signal in low frequencies f.

Such a high input impedance can be obtained by using a large electrode. However, a hearing aid is a small electronic device, and therefore the use of large electrodes should be avoided.

Moreover, as shown in FIG. 2, an input referred noise, at the level of the electrode, comprises white noise, which is present in all frequencies, and flicker noise, which is dominant in low frequencies, under a flicker noise corner frequency. The EEG signals being of low frequencies, it is therefore necessary to reduce the input referred noise.

It is known, to avoid flicker noise, to use a chopper circuit which moves the EEG signal in higher frequencies, above the flicker noise corner frequency. However, the switching activity of the chopper circuit reduces the input impedance of the capacitive electrode.

To increase the input impedance, it is known to apply a voltage buffer before or after the chopper circuit, this voltage buffer comprising a plurality of MOSFETs (Metal-Oxide-Semiconductor Field-Effect Transistor). However, to obtain a low flicker noise in the voltage buffer, larges MOSFETs are required, since in a MOSFET, the flicker noise power is inversely proportional to the gate area of the MOSFET. Such larges MOSFETs should nevertheless be avoided in a hearing aid, wherein there is not a lot of space for electronic components.

Moreover, it is known, to avoid flicker noise, to use a switched biasing circuit 310 shown in FIG. 3, configured to switch an MOSFET 320 of a voltage buffer between weak, moderate or strong inversion (also called saturation), by switching the voltage at the gate terminal GT of the MOSFET 320.

The switched biasing circuit 310 comprises a first switch 312 and a second switch 314, the first switch 312 being located between the gate terminal and a supply voltage source and being controlled by a first control signal, and the second switch 314 being located between the gate terminal and the electrode and being controlled by a second control signal, so that when the first switch 312 is in a closed state, the second switch 314 is in an open state and the gate terminal is at the supply source voltage $V_{DD}$, and when the first switch 312 is in the open state, the second switch 314 is in a closed state and the gate terminal is at the EEG signal voltage $V_{sig}$.

The voltage at the gate terminal GT of the MOSFET 320 is therefore modulated to turn off the MOSFET 320 and reduce the noise. The on/off cycle allows to lower the overall probability of the charges being trapped, as when a transistor is turned on, the charges can be trapped and released in an interface of the transistor between the drain terminal and the source terminal of the transistor, and when the transistor is turned off, the probability of the charges stuck in the interface being released increases and no new charge will be trapped. Reducing the overall probability of the charges being trapped reduces the flicker noise.

However, the switched biasing circuit 310 reduces the input impedance of the voltage buffer, causing an unwanted attenuation of the EEG signal.

There is therefore a need for a solution to provide a high input impedance at the level of the electrode while reducing the input referred noise.

SUMMARY

An aspect of the disclosure is to provide a hearing aid, comprising;
 at least one sensor configured to provide a sensing signal, and
 at least one sensing signal processing circuit, comprising a first switch bias buffer circuit comprising:
  a first voltage buffer configured to receive the sensing signal and to provide a first buffer signal at a reduced impedance node, and
  a first switching circuit configured to modulate the output voltage of the first voltage buffer.

Modulating the output voltage of the first voltage buffer allows reducing the input referred noise while maintaining a high input impedance at the level of the sensor.

The first voltage buffer may comprise a first MOSFET transistor having a first terminal, a second terminal and a third terminal, the first terminal voltage being the output voltage of the first voltage buffer, the first switching circuit being configured to switch the voltage at the first terminal between a reference voltage and the voltage at the output of the first switch bias buffer circuit.

The first MOSFET transistor may be a common-drain MOSFET transistor, the first terminal being the source terminal of the common-drain MOSFET transistor.

The voltage at the source terminal of the first MOSFET is therefore modulated to turn off the first MOSFET and reduce the noise, without reducing the input impedance at the level of the sensor.

The at least one sensing signal processing circuit may further comprise a second switch bias buffer circuit, comprising:
 a second voltage buffer configured to receive the sensing signal and to provide a second buffer signal at a second reduced impedance node, and
 a second switching circuit configured to modulate the output voltage of the second voltage buffer,
second switch bias buffer circuit being configured to operate in reverse with respect to the first switch bias buffer circuit.

The second voltage buffer may comprise a second MOSFET transistor having a first terminal, a second terminal and a third terminal, the second switching circuit being configured to switch the voltage at the first terminal of said second MOSFET transistor:
  to the voltage at the output of the second switch bias buffer circuit when the first switching circuit switches the voltage at the first terminal of the first MOSFET transistor to the reference voltage, and
  to the reference voltage when the first switching circuit switches the voltage at the first terminal of the first MOSFET transistor to the voltage at the output of the first switch bias buffer circuit.

The at least one sensing signal processing circuit may further comprise a first bias circuit, the first bias circuit being configured to reduce the flicker noise at the first terminal of the first MOSFET transistor, the first bias circuit comprising:
  a first current mirror, comprising two transistors, and
  a first bias switch configured the switch the voltages at the gate terminals of the two transistors of the first current mirror between a bias node voltage and a supply voltage.

Such a switching allows reducing the flicker noise at the first terminal of the first MOSFET transistor of the first voltage buffer, without resorting to the use of large transistors at the level of the current mirror.

The at least one sensing signal processing circuit may further comprise a second bias circuit, the second bias circuit being configured to reduce the flicker noise at the first terminal of the second MOSFET transistor, the second bias circuit comprising:
  a second current mirror, comprising two transistors, and
  a second bias switch configured to switch the voltages at the gate terminals of the two transistors of the second current mirror between the bias node voltage and the supply voltage, in a reverse manner with respect to the first bias switch.

Such a sensing signal processing circuit maintains a high input impedance, as the switch bias is moved away from input, but also offers continuous signal sensing and severely reduced kickback (due to the first and second switch bias buffer circuits), and a gain of space thanks to the first and second bias circuits.

The at least one sensing signal processing circuit may further comprise a chopper amplifier, configured to:
  modulate the frequency of the output signal of the at least one sensing signal processing circuit,
  amplify the modulated output signal, and
  demodulate the frequency of the amplified signal.

The chopper amplifier allows to reduce the flicker noise by increasing the frequency of the output signal (as the flicker noise is not present in high frequencies).

The hearing aid may be configured to compensate a hearing loss of a user of the hearing aid, and may comprise:
  a microphone configured to receive an acoustic wave and provide an audio signal based on the acoustic wave,
  a signal processor unit configured to process the audio signal and provide a processed audio signal, and
  an output transducer configured to output the processed audio signal to the user, and wherein the signal processor unit is configured to process the audio signal based on the output signal of the at least one sensing signal processing circuit or is configured to adapt a hearing profile stored within a memory of the hearing aid based on the output signal of the at least one sensing signal processing circuit.

The hearing aid may comprise:
  an in-the-ear unit;
  a behind-the-ear unit;
  a communication link configured to provide an electrical connection between the in-the-ear unit and the behind-the-ear unit, and
  a processor unit configured to receive the output signal of the at least one sensing signal processing circuit via the communication link,
wherein the at least one sensor is arranged in the in-the-ear unit, and the processor unit is arranged in the behind-the-ear unit of the hearing aid.

The communication link can be a communication bus or a wireless communication link.

The hearing aid may comprise a housing that includes the at least one sensor and the at least one sensing signal processing circuit.

The at least one sensor may be a capacitive sensor configured to provide a capacitive sensing signal, such as a capacitive electrode configured to provide a bio response signal, such as an EEG signal, an Electrocardiogram (ECG) signal, an electrooculography (EOG) signal or a muscular activity signal, or a microphone. The at least one sensor may also be a resistive electrode.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

DETAILED DESCRIPTION

Figure 1:
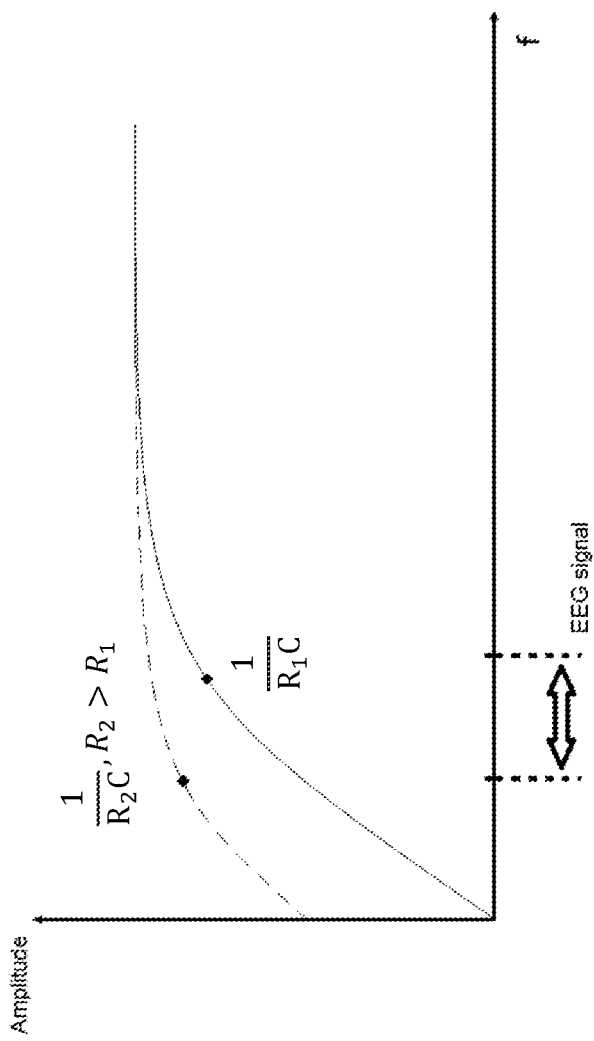
FIG. 1 schematically shows a curve representing the magnitude response of an exemplary EEG signal acquisition system as a function of the frequency, FIG. 2 schematically shows a curve representing the power spectral density of an exemplary input referred noise signal as a function of the frequency, FIG. 3 schematically shows a switched biasing circuit according to the prior art, FIG. 4 schematically shows an EEG signal processing circuit of a hearing aid, according to an exemplary embodiment of the invention, FIG. 5A-5E schematically shows voltage variations over time of several signals related to the EEG signal processing circuit 400 of FIG. 4, FIG. 6-10 schematically show EEG signal processing circuits of a hearing aid, according to other exemplary embodiments of the invention, and FIG. 11A-11F schematically shows voltage variations over time of several signals related to the EEG signal processing circuit of FIG. 7.
Figure 2:
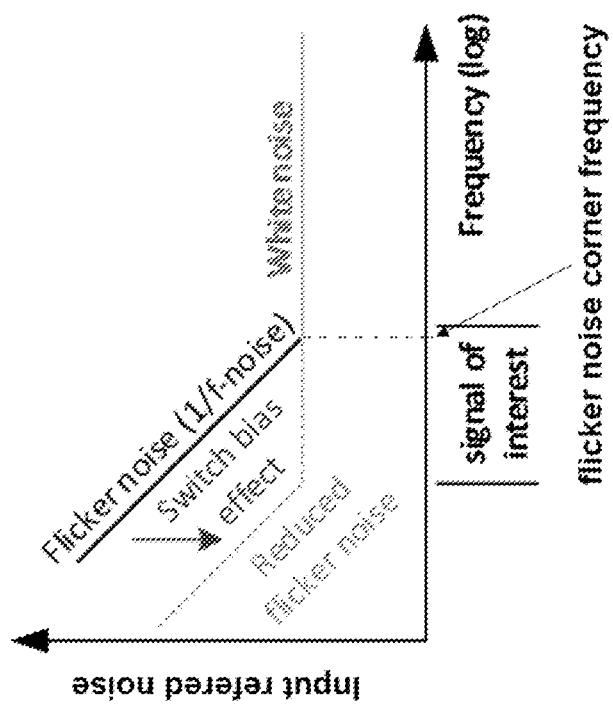
Figure 3:
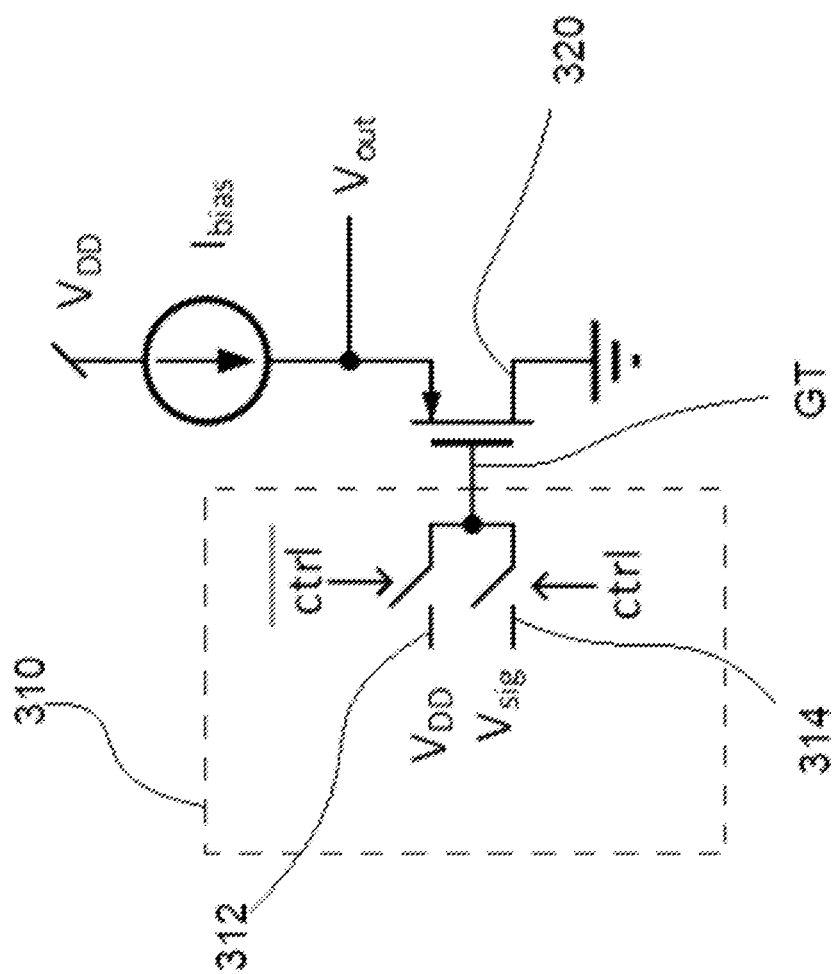

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the hearing instrument are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

The electronic hardware may include micro-electronic-mechanical systems (MEMS), integrated circuits (e.g. application specific), microprocessors, microcontrollers, digital signal processors (DSPs), field programmable gate arrays (FPGAs), programmable logic devices (PLDs), gated logic, discrete hardware circuits, printed circuit boards (PCB) (e.g. flexible PCBs), and other suitable hardware configured to perform the various functionality described throughout this disclosure, e.g. sensors, e.g. for sensing and/or registering physical properties of the environment, the device, the user, etc. Computer program shall be construed broadly to mean instructions, instruction sets, code, code segments, program code, programs, subprograms, software modules, applications, software applications, software packages, routines, subroutines, objects, executables, threads of execution, procedures, functions, etc., whether referred to as software, firmware, middleware, microcode, hardware description language, or otherwise.

A hearing instrument may refer to a hearing aid adapted to improve or augment the hearing capability of a user by receiving an acoustic signal from a user's surroundings, generating a corresponding audio signal, possibly modifying the audio signal and providing the possibly modified audio signal as an audible signal to at least one of the user's ears. 'Improving or augmenting the hearing capability of a user' may include compensating for an individual user's specific hearing loss.

The "hearing instrument" may further refer to a device such as a hearable, an earphone or a headset adapted to receive an audio signal electronically, possibly modifying the audio signal and providing the possibly modified audio signals as an audible signal to at least one of the user's ears.

Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user. The hearing instrument is adapted to be worn in any known way. This may include i) arranging a unit of the hearing instrument behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing instrument entirely or partly in the pinna and/or in the ear canal of the user such as in an In-the-Ear type hearing aid or In-the-Canal/Completely-in-Canal type hearing aid, or iii) arranging a unit of the hearing instrument attached to a fixture implanted into the skull bone such as in a Bone Anchored Hearing Aid or a Cochlear Implant, or iv) arranging a unit of the hearing instrument as an entirely or partly implanted unit such as in a Bone Anchored Hearing Aid or a Cochlear Implant. The hearing instrument may be implemented in one single unit (housing) or in a number of units individually connected to each other.

The hearing aid typically comprises:
a microphone configured to receive an acoustic wave and provide an audio signal based on the acoustic wave,
a signal processor unit configured to process the audio signal and provide a processed audio signal,
an output transducer configured to output the processed audio signal to the user.

The signal processor unit is configured to process the audio signal based on the output signal of the at least one EEG signal processing circuit or is configured to adapt a hearing profile stored within a memory of the hearing aid based on the output signal of the at least one EEG signal processing circuit.

The hearing aid can for example comprise:
an in-the-ear unit;
a behind-the-ear unit;
a communication link configured to provide an electrical connection between the in-the-ear unit and the behind-the-ear unit (the communication link being a communication bus or a wireless communication link),
a processor unit configured to receive the output signal of the at least one EEG signal processing circuit via the communication link.

Moreover, the hearing aid typically comprises a housing that includes at least one sensor and at least one sensing signal processing circuit, as the electrodes and the EEG signal processing circuits described below. The at least one sensor and the at least one sensing signal processing circuit can be arranged in the in-the-ear unit, the processor unit being arranged in the behind-the-ear unit of the hearing aid.

The at least one sensor is configured to provide a sensing signal, and the at least one sensing signal processing circuit comprises a first switch bias buffer circuit. The first switch bias buffer circuit comprises a first voltage buffer configured to receive the sensing signal and to provide a first buffer signal at a reduced impedance node, and a first switching circuit configured to modulate the output voltage of the first voltage buffer.

The hearing aid may comprise a plurality of electrodes, each electrode being configured to provide an EEG signal, i.e. an electrical signal representing a person's brain electrical activity, by providing an electrical stimulation to a user of the hearing aid and/or measuring a bio response signal of the user. Specifically, the hearing aid may comprise at least two electrodes, a reference electrode and a measurement electrode.

The reference electrode has a stable and well-known electrode potential and can be used as a reference for measurement by the measurement electrode.

Typically, the hearing aid comprises the reference electrode and a plurality of measurement electrodes.

Each electrode can be a capacitive electrode, comprising a capacitive sensor, or a resistive electrode, comprising a resistive sensor.

Moreover, the hearing aid may comprise a plurality of EEG signal processing circuits, each EEG signal processing circuit being directly connected to a different electrode of the plurality of electrodes. Each electrode has therefore an associated EEG signal processing circuit.

It is then possible to use the processed EEG signals to control or adjust signal processing in the hearing aid.

Each EEG signal processing circuit comprises a first switch bias buffer circuit, the first switch bias buffer circuit comprising a first voltage buffer configured to receive the EEG signal and to provide a first buffer signal at a reduced impedance node, and a first switching circuit configured to modulate the output voltage of the first voltage buffer.

Modulating the output voltage of the first voltage buffer allows reducing the input referred noise while maintaining a high input impedance at the level of the electrode.

Figure 4:
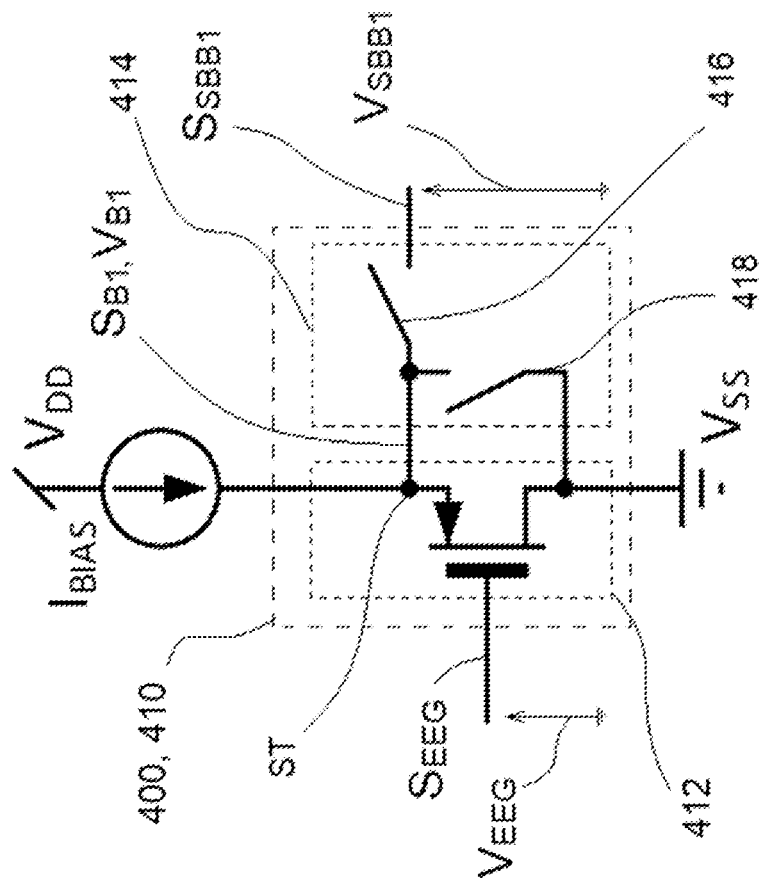

FIG. 4 schematically shows an EEG signal processing circuit 400 of a hearing aid, according to an exemplary embodiment of the invention.

More specifically, the EEG signal processing circuit 400 comprises a first switch bias buffer circuit 410.

The first switch bias buffer circuit 410 comprises a first voltage buffer 412 configured to receive the EEG signal $S_{EEG}$ outputted by the corresponding electrode, and to provide a first buffer signal $S_{B1}$ at a reduced impedance node ST.

Moreover, the first switch bias buffer circuit 410 comprises a first switching circuit 414 configured to modulate the output voltage $V_{B1}$ of the first voltage buffer 412.

The first voltage buffer 412 typically comprises a first MOSFET transistor having a first terminal, a second terminal and a third terminal, the first terminal voltage being the output voltage $V_{B1}$ of the first voltage buffer 412.

As an alternative, the first voltage buffer 412 can comprise a plurality of MOSFET transistors, configured as an amplifier.

The first switching circuit 414 is configured to switch the voltage $V_{B1}$ at the first terminal between a reference voltage $V_{SS}$ and the voltage $V_{SBB1}$ at the output of the first switch bias buffer circuit 410 (which is also the output of the first switching circuit 414).

The reference voltage $V_{SS}$ is typically the ground voltage.

In FIG. 4, the first MOSFET transistor is a common-drain MOSFET transistor, the first terminal being the source terminal ST of the common-drain MOSFET transistor. The first voltage buffer 412 can be called in that case a single stage common-drain MOSFET amplifier.

The first switching circuit 414 comprises a first switch 416 and a second switch 418. The first switch 416 is typically located between the first terminal ST of the first MOSFET transistor and the output of the first switch bias buffer circuit 410. Specifically, a first terminal of the first switch 416 is directly and electrically connected to the first terminal ST of the first MOSFET transistor and a second terminal of the first switch 416 is directly and electrically connected to the output of the first switch bias buffer circuit 410.

The second switch 418 is typically located between the first terminal ST of the first MOSFET transistor and the ground. Specifically, a first terminal of the second switch 418 is directly and electrically connected to the first terminal ST of the first MOSFET transistor and a second terminal of the first switch 418 is directly and electrically connected to the ground.

The first switch 416 may be periodically controlled by a first control signal $clk_a$, and the second switch by a second control signal $clk_b$, so that when the first switch 416 is in a closed state, the second switch 418 is in an open state and the first terminal ST is at the voltage $V_{SBB1}$ of the output of the first switch bias buffer circuit 410, and when the first switch 416 is in the open state, the second switch 418 is in a closed state and the first terminal ST is at the reference voltage $V_{SS}$.

Thereby the first MOSFET transistor is periodically switched between operating in saturation and being turned off.

The frequency of the first control signal $clk_a$ and the second control signal $clk_b$ is typically greater than the frequency of the flicker noise corner.

When the first MOSFET transistor is operating in saturation, flicker noise is built up by the accumulation of trapped charges in the interface between the MOSFET gate oxide and the MOSFET channel. When turning off the first MOSFET transistor, no further charges are trapped in this interface and instead trapped charges are released over time.

The effect of switching the operating region of the first MOSFET transistor is that the amount of time during which the flicker noise is generated is reduced by a factor given from the duty-cycle the transistor is on. Furthermore, since the trapping of charges is temporal (i.e. built up over time) and not instantaneous, the flicker noise will be reduced by a factor larger than the duty cycle applied. When the duty cycle is on 0.5 or 50%, the amount of time where flicker noise is generated is typically reduced by two, and can be further reduced for lower duty cycles.

Therefore, the voltage at the source terminal ST of the first MOSFET is modulated to turn off the first MOSFET and reduce the noise, without reducing the input impedance at the level of the electrode.

A high impedance input bias (not represented), which can be made in several different ways, is needed together with the bias current $I_{bias}$ to put the source follower transistors in their intended inversion region.

Figure 5:
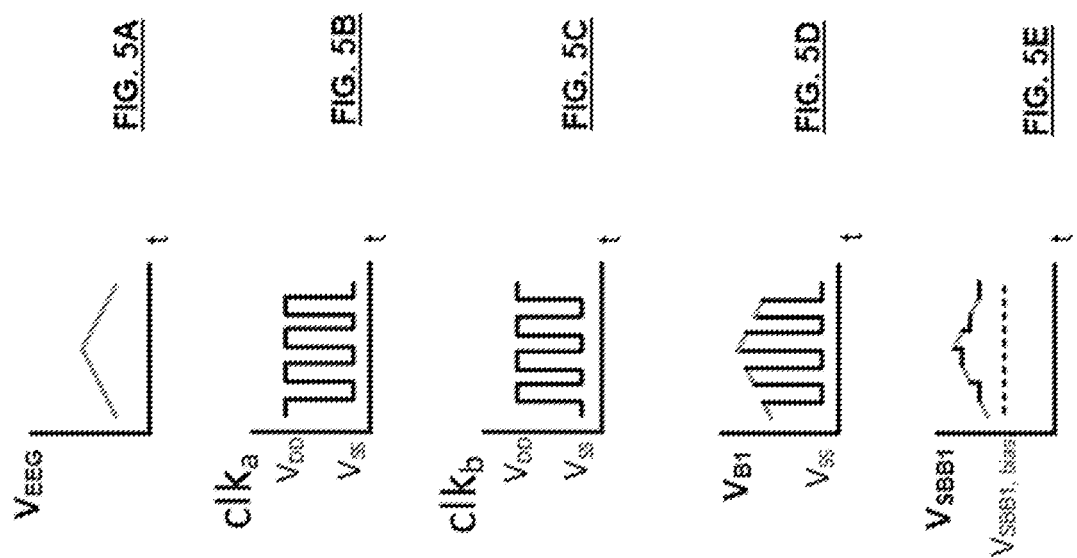

FIG. 5A-5E shows voltage variations over time of several signals related to the EEG signal processing circuit 400 of FIG. 4. More specifically, FIG. 5A is a graph representing the voltage $V_{EEG}$ of the EEG signal $S_{EEG}$ versus time, FIG. 5B is a graph representing the voltage of the first control signal $clk_a$ of the first switch 416 versus time, FIG. 5C is a graph representing the voltage of the second control signal $clk_b$ of the second switch 418 versus time, FIG. 5D is a graph representing the voltage $V_{B1}$ at the first terminal versus time, and FIG. 5E is a graph representing the voltage $V_{SBB1}$ at the output of the first switch bias buffer circuit 410 versus time.

The first control signal $clk_a$ and the second switch by a second control signal $clk_b$ switch between two values and are in antiphase to one another. Specifically, the two values are the supply source voltage $V_{DD}$ and the reference voltage $V_{SS}$.

The supply voltage $V_{DD}$ is a voltage which is internal to the hearing aid, e.g. the battery voltage or a voltage derived from the battery voltage.

When the first control signal $clk_a$ is at the supply source voltage $V_{DD}$, the second control signal $clk_b$ is at the reference voltage $V_{SS}$, the voltage $V_{B1}$ at the first terminal follows the voltage $V_{EEG}$ of the EEG signal $S_{EEG}$, and the voltage $V_{SBB1}$ at the output of the first switch bias buffer is equal to the voltage $V_{EEG}$ of the EEG signal $S_{EEG}$. At a given time at which the first control signal $clk_a$ is at the supply source voltage $V_{DD}$, the shift between the value of the voltage $V_{B1}$ at the first terminal and the voltage $V_{EEG}$ of the EEG signal $S_{EEG}$ is intrinsic to the source follower configuration of the transistor, requiring that the voltage $V_{B1}$ needs to be greater than the voltage $V_{EEG}$ at the gate terminal to turn on the transistor and measure the EEG signal.

When the first control signal $clk_a$ is at the reference voltage $V_{SS}$, the second control signal $clk_b$ is at the supply source voltage $V_{DD}$, and the voltage $V_{B1}$ at the first terminal is equal to the reference voltage $V_{SS}$, and the voltage $V_{SBB1}$ at the output of the first switch bias buffer is kept constant at the value of the reference voltage $V_{SS}$. As explained above, this turns off the transistor and therefore allows reducing the flicker noise.

In FIG. 4, the first terminal ST is connected to a bias current $I_{BIAS}$ source which represents an ideal component, that does not induce noise.

Instead of a single stage common-drain MOSFET amplifier, another kind of transistor can be used for the first voltage buffer 412, such as a Negative Metal-Oxide Semiconductor (NMOS) transistor. The use of the NMOS transistor requires a biasing of the gate terminal of the NMOS transistor, the bias current $I_{BIAS}$ source being located between the source terminal of the NMOS transistor and the ground, the drain terminal of the NMOS transistor being connected to the supply source voltage $V_{DD}$, a switch being located between the source terminal and the drain terminal of the NMOS transistor, and another switch being located between the source terminal of the NMOS transistor and the output of the switch bias buffer circuit. However, this configuration requires to bias the body of the hearing aid user at a higher potential.

Figure 6:
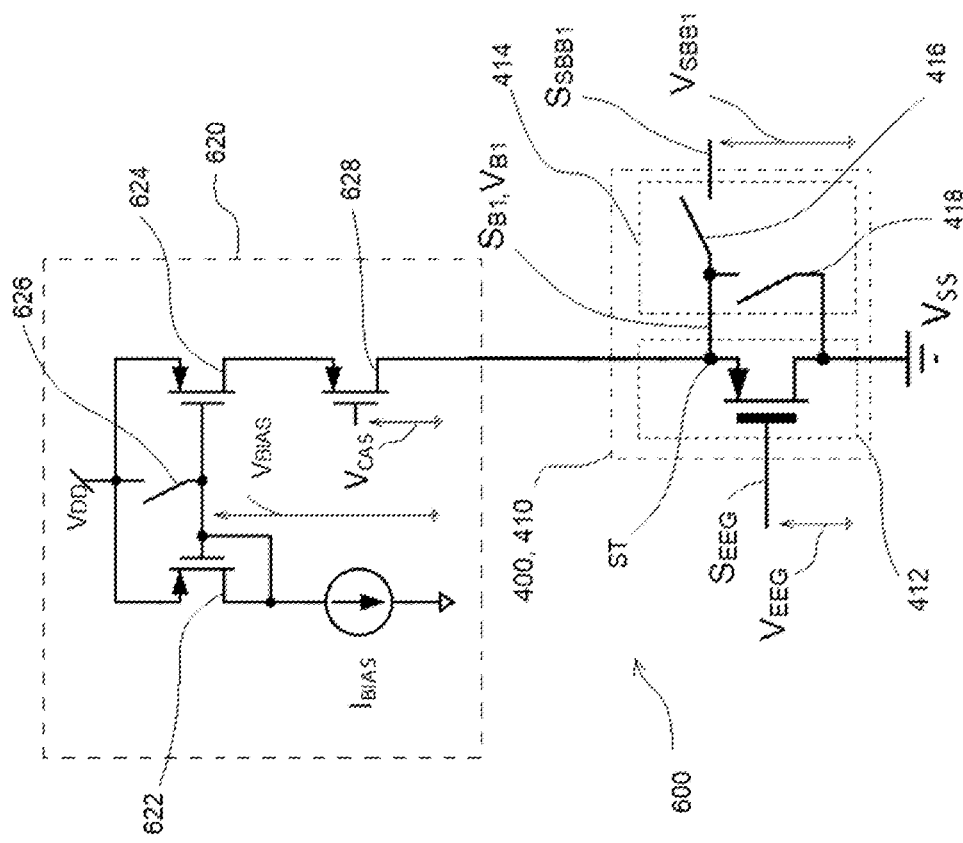

FIG. 6 schematically shows an EEG signal processing circuit 600 of a hearing aid, according to another exemplary embodiment of the invention.

EEG signal processing circuit 600 comprises the first switch bias buffer circuit 410 described with reference to FIG. 4, comprising the first voltage buffer 412 configured to receive the EEG signal $S_{EEG}$ and to provide a first buffer signal $S_{B1}$ at a reduced impedance node, and the first switching circuit 414 configured to modulate the output voltage $V_{B1}$ of the first voltage buffer 412.

Moreover, the EEG signal processing circuit 600 comprises a first bias circuit 620, the first bias circuit 620 being configured to reduce the flicker noise at the first terminal ST of the first MOSFET transistor.

The first bias circuit 620 comprises a first current mirror comprising two transistors 622, 624, which can be e.g. PMOS transistors.

When the two transistors 622, 624 have the same size, the bias current $I_{BIAS}$ is "propagated" to the first terminal ST of the first MOSFET transistor of the first voltage buffer 412 (or at least to the drain terminal of the second transistor 624 of the first current mirror).

Moreover, the first bias circuit 620 comprises a first bias switch 626 configured to switch the voltages at the gate terminals of the two PMOS transistors 622, 624 of the first current mirror between a bias node voltage $V_{BIAS}$ at the gate terminals of the two transistors 622, 624 and the supply source voltage $V_{DD}$, so that when the first voltage buffer 412 is turned off, the second transistor 624 of the first current mirror is also turned off (the second switch 418 and the first bias switch 626 are controlled by the second control signal $clk_b$).

Such a switching allows reducing the flicker noise at the first terminal of the first MOSFET transistor of the first voltage buffer 412.

The first bias circuit 620 can also comprises a "cascode" transistor 628, also called "common gate" transistor 628, to help control the bias voltage at the output and have a better gain between the input and the output.

A high impedance input bias (not represented), which can be made in several different ways, is needed together with the bias current Ibias to put the source follower transistors in their intended inversion region.

Figure 7:
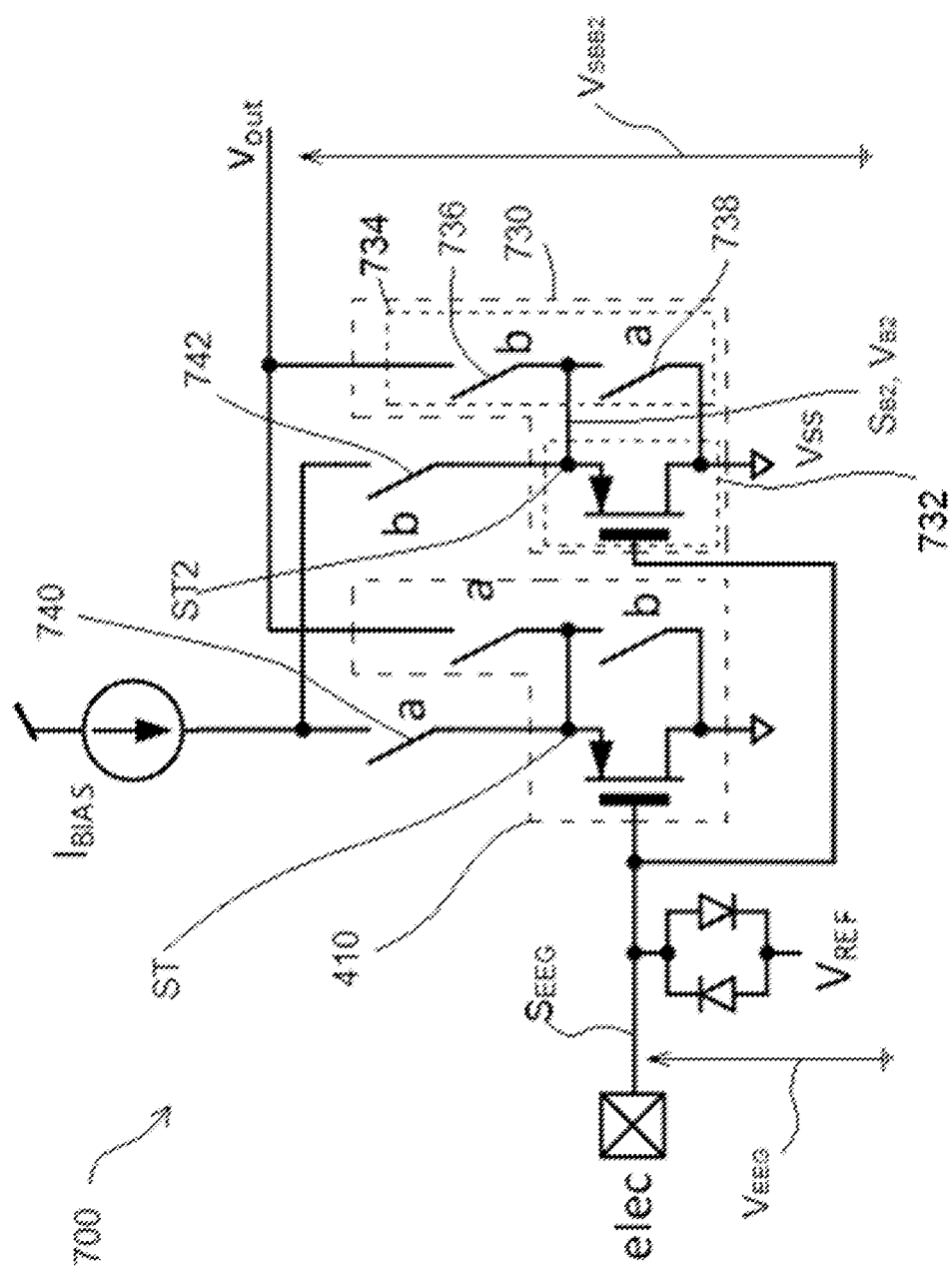

FIG. 7 schematically shows an EEG signal processing circuit 700 of a hearing aid, according to another exemplary embodiment of the invention.

The EEG signal processing circuit 700 comprises the first switch bias buffer circuit 410 described with reference to FIG. 4, comprising the first voltage buffer 412 configured to receive the EEG signal $S_{EEG}$ and to provide a first buffer signal $S_{B1}$ at a reduced impedance node, and the first switching circuit 414 configured to modulate the output voltage $V_{B1}$ of the first voltage buffer 412.

Moreover, the EEG signal processing circuit 700 can comprise the first bias circuit 620 described with reference to FIG. 6 (not shown in FIG. 7).

Furthermore, the EEG signal processing circuit 700 comprises a second switch bias buffer circuit 730, which is connected in parallel to the first switch bias buffer circuit 410.

The second switch bias buffer circuit 730 comprises a second voltage buffer 732 configured to receive the EEG signal $S_{EEG}$ and to provide a second buffer signal $S_{B2}$ at a second reduced impedance node.

The second voltage buffer 732 typically comprises a second MOSFET transistor having a first terminal, a second terminal and a third terminal, the first terminal voltage being the output voltage $V_{B2}$ of the second voltage buffer 732.

The second switching circuit 734 is configured to switch the voltage $V_{B2}$ at the first terminal of the second voltage buffer 732 between the reference voltage $V_{SS}$ and the voltage $V_{SBB2}$ at the output of the second switch bias buffer circuit 730 (which is also the output of the first switching circuit 734).

In FIG. 7, the second MOSFET transistor is a common-drain MOSFET transistor, the first terminal being the source terminal ST of the common-drain MOSFET transistor. However, as for the first MOSFET transistor, another kind of transistor can be used for the second MOSFET transistor.

Moreover, the second switch bias buffer circuit 730 comprises a second switching circuit 734 configured to modulate the output voltage $V_{B2}$ of the second voltage buffer 732.

The second switching circuit 734 has the same structure as the first switching circuit 414. The second switching circuit 734 therefore comprises a first switch 736 typically located between the first terminal ST2 of the second MOSFET transistor and the output of the second switch bias buffer circuit 730, and a second switch 738 typically located between the first terminal ST2 of the second MOSFET transistor and the ground.

The second switch bias buffer circuit 730 is configured to operate in reverse with respect to the first switch bias buffer circuit 410.

Specifically, the second switching circuit 734 is configured to switch the voltage at the first terminal ST2 of said second MOSFET transistor:
  to the voltage at the output of the second switch bias buffer circuit when the first switching circuit switches the voltage at the first terminal of the first MOSFET transistor to the reference voltage, and
  to the reference voltage when the first switching circuit switches the voltage at the first terminal of the first MOSFET transistor to the voltage at the output of the first switch bias buffer circuit.

Moreover, the EEG signal processing circuit 700 comprises a first bias current source switch 740 and a second bias current source switch 742. The first bias current source switch 740 is located between the bias current $I_{BIAS}$ source and the first terminal ST of the first MOSFET transistor (meaning that a first terminal of the first bias current source switch 740 is directly and electrically connected to the bias current $I_{BIAS}$ source and a second terminal of the first bias current source switch 740 is directly and electrically connected to first terminal ST of the first MOSFET transistor), and the second bias current source switch 742 is located between the bias current $I_{BIAS}$ source and the first terminal ST2 of the second MOSFET transistor (meaning that a first terminal of the second bias current source switch 742 is directly and electrically connected to the bias current $I_{BIAS}$ source and a second terminal of the second bias current source switch 742 is directly and electrically connected to first terminal ST2 of the second MOSFET transistor).

The first bias current source switch 740 and the second bias current source switch 742 are controlled in antiphase, so that the first switch bias buffer circuit 410 and the second switch bias buffer circuit 730 are operated in parallel in a so called "ping-pong manner", meaning that when the first switch bias buffer circuit 410 is turned on, the second bias current source switch 742 is turned off, and when the first switch bias buffer circuit 410 is turned off, the second bias current source switch 742 is turned on. This allows reducing the flicker noise in the switch bias buffer circuit 410, 730 that is turned off. By doing this quickly and periodically, the overall flicker noise of the two switches bias buffer circuit 410, 730 should be reduced.

A high impedance input bias is needed together with the bias current Ibias to put the source follower transistors in their intended inversion region. The high impedance bias can be made in several different ways but is made in this example with back to back diodes.

FIG. 11A-11F shows voltage variations over time of several signals related to the EEG signal processing circuit 700 of FIG. 7. More specifically, FIG. 11A is a graph representing the voltage $V_{EEG}$ of the EEG signal $S_{EEG}$ versus time, FIG. 11B is a graph representing the voltage of the first control signal $clk_a$ of the first switch 416 versus time, FIG. 11C is a graph representing the voltage of the second control signal $clk_b$ of the second switch 418 versus time, FIG. 11D is a graph representing the voltage $V_{B1}$ at the output of the first voltage buffer versus time, FIG. 11E is a graph representing the voltage $V_{B2}$ at the output of the second voltage buffer 732 versus time, and FIG. 11F is a graph representing the voltage $V_{OUT}$ at the output of the EEG signal processing circuit 700 versus time.

The first control signal $clk_a$ and the second switch by a second control signal $clk_b$ switch between two values and are in antiphase to one another. Specifically, the two values are the supply source voltage $V_{DD}$ and the reference voltage $V_{SS}$.

When the first control signal $clk_a$ is at the supply source voltage $V_{DD}$, the second control signal $clk_b$ is at the reference voltage $V_{SS}$, the voltage $V_{B1}$ at the output of the first voltage buffer follows the voltage $V_{EEG}$ of the EEG signal $S_{EEG}$, the voltage $V_{B2}$ at the output of the second voltage buffer 732 is equal to the reference voltage $V_{SS}$, and the voltage $V_{OUT}$ at the output of the EEG signal processing circuit 700 is equal to the voltage $V_{B1}$ at the output of the first voltage buffer.

When the first control signal $clk_a$ is at the reference voltage $V_{SS}$, the second control signal $clk_b$ is at the supply source voltage $V_{DD}$, the voltage $V_{B1}$ at the output of the first voltage buffer is equal to the reference voltage $V_{SS}$, the voltage $V_{B2}$ at the output of the second voltage buffer 732 follows the voltage $V_{EEG}$ of the EEG signal $S_{EEG}$, and the voltage $V_{OUT}$ at the output of the EEG signal processing circuit 700 is equal to the voltage $V_{B2}$ at the output of the second voltage buffer 732.

As a result, the output of the EEG signal processing circuit 700 always follows the voltage $V_{EEG}$ of the EEG signal $S_{EEG}$.

Figure 8:
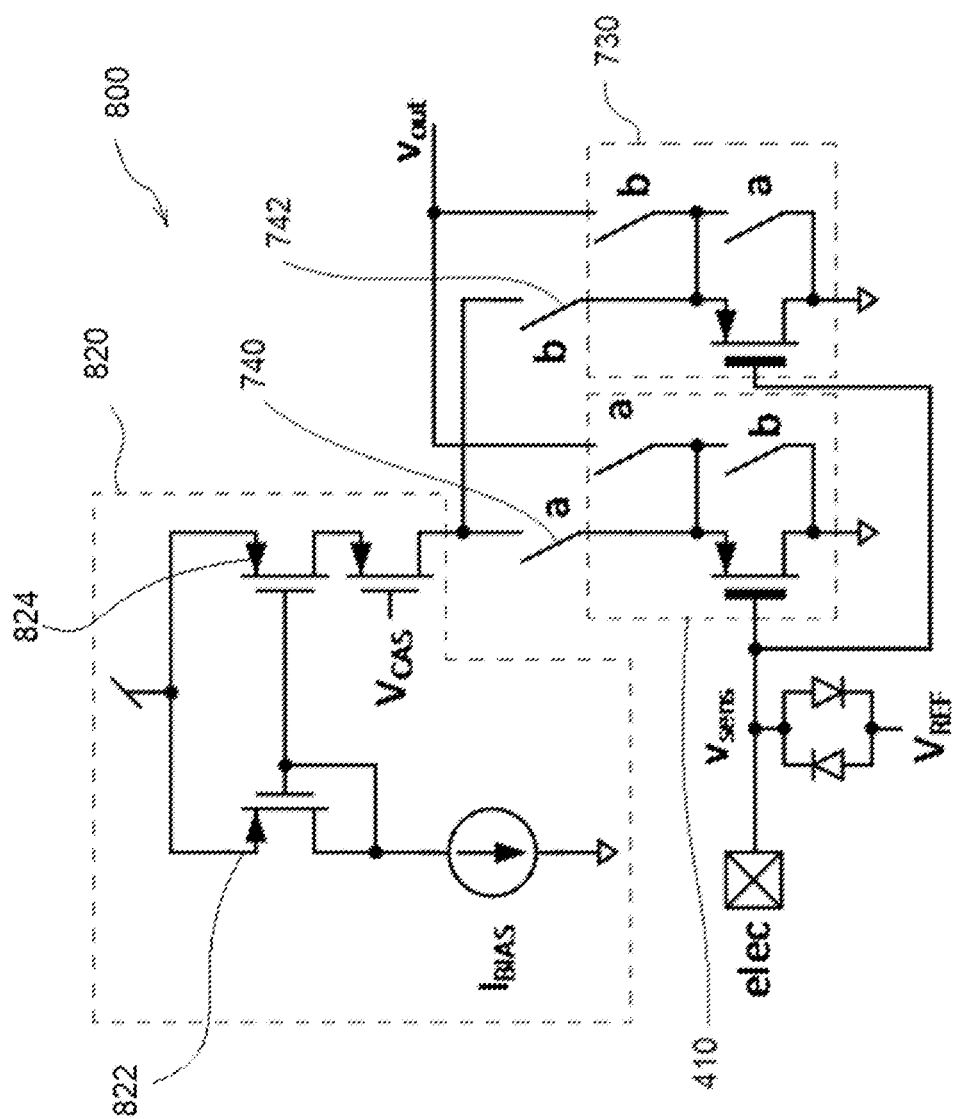

FIG. 8 schematically shows an EEG signal processing circuit 800 of a hearing aid, according to another exemplary embodiment of the invention. The EEG signal processing circuit 800 comprises the first switch bias buffer circuit 410, the second switch bias buffer circuit 700, the first bias current source switch 740 and the second bias current source switch 742 described with reference to FIG. 7, and a first bias circuit 820.

The first bias circuit 820 comprises a first current mirror comprising two transistors 822, 824, which can be e.g. PMOS transistors.

Figure 9:
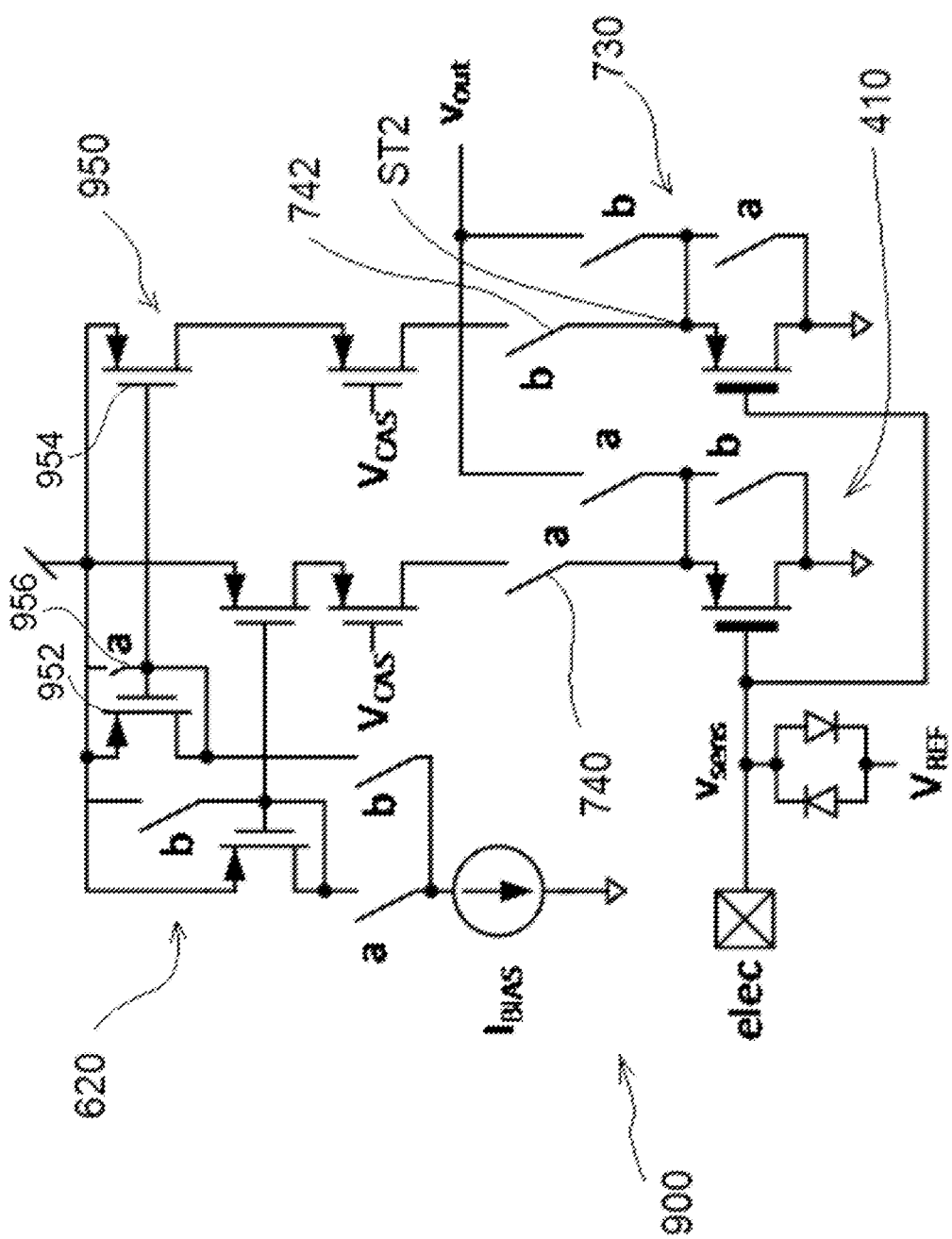

FIG. 9 schematically shows an EEG signal processing circuit 900 of a hearing aid, according to another exemplary embodiment of the invention. The EEG signal processing circuit 800 comprises the first switch bias buffer circuit 410, the second switch bias buffer circuit 700, the first bias current source switch 740 and the second bias current source switch 742 described with reference to FIG. 7, and the first bias circuit 620 described in reference to FIG. 6.

Moreover, the EEG signal processing circuit 900 comprises a second bias circuit 950, the second bias circuit 950 being configured to reduce the flicker noise at the first terminal ST2 of the second MOSFET transistor.

The second bias circuit 950 comprises a second current mirror, comprising two transistors 952, 954, which can be e.g. PMOS transistors.

Moreover, the second bias circuit 950 comprises a second bias switch 956 configured to switch the voltages at the gate terminals of the two transistors 952, 954 of the second current mirror between the bias node voltage and the supply voltage, in a reverse manner with respect to the first bias switch 626.

The EEG signal processing circuit 900 maintains a high input impedance, as the switch bias is moved away from input, but also offers continuous signal sensing and severely reduced kickback (due to the first and second switch bias buffer circuits 410, 730), and allows reducing the size of the transistors thanks to the first and second bias circuits 620, 950.

Figure 10:
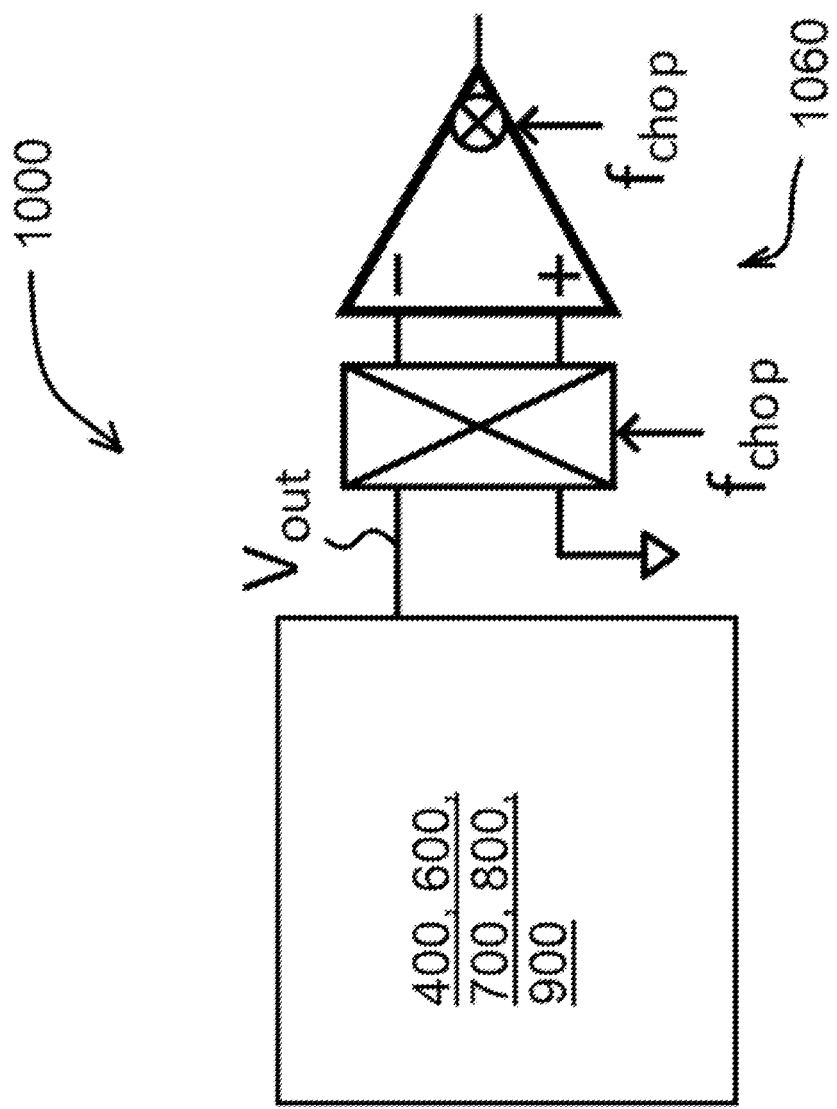

FIG. 10 schematically shows an EEG signal processing circuit 1000 of a hearing aid, according to another exemplary embodiment of the invention.

The EEG signal processing circuit 1000 can e.g. be the EEG signal processing circuit 400 described with reference to FIG. 4, the EEG signal processing circuit 600 described with reference to FIG. 6, the EEG signal processing circuit 700 described with reference to FIG. 7, the EEG signal processing circuit 800 described with reference to FIG. 8, or the EEG signal processing circuit 900 described with reference to FIG. 9.

Moreover, FIG. 10 shows a chopper amplifier 1060, configured to:
  modulate the frequency of the output signal $V_{out}$ of the EEG signal processing circuit 400, 600, 700, 800, 900,
  amplify the modulated output signal, and
  demodulate the frequency of the amplified signal.

The chopper amplifier 1060 allows to reduce the flicker noise by increasing the frequency of the output signal $V_{out}$ (as the flicker noise is not present in high frequencies).

The chopper amplifier 1060 of FIG. 10 is a single ended chopper amplifier. However, it is possible to use a differential implementation with two switch bias circuits.

Each of the EEG signal processing circuits described in FIGS. 4 to 10 can be replaced by another sensing signal processing circuit, comprising the same elements, but configured to receive a sensing signal provided by a sensor, such as a capacitive sensor configured to provide a capacitive sensing signal, such as a capacitive electrode configured to provide a bio response signal, such as an EEG signal, an ECG signal, an EOG signal or a muscular activity signal, or a microphone.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more". Unless specifically stated otherwise, the term "some" refers to one or more.

The invention claimed is:

1. A hearing aid comprising:
   at least one sensor configured to provide a sensing signal, and
   at least one sensing signal processing circuit, comprising a first switch bias buffer circuit comprising:
   a first voltage buffer configured to receive the sensing signal and to provide a first buffer signal at a reduced impedance node, and
   a first switching circuit configured to modulate the output voltage of the first voltage buffer,
   wherein the first voltage buffer comprises a first MOSFET transistor having a first terminal, a second terminal and a third terminal,
   the first terminal voltage being the output voltage of the first voltage buffer,
   the first switching circuit being configured to switch the voltage at the first terminal between a reference voltage and the voltage at the output of the first switch bias buffer circuit
   wherein the at least one sensing signal processing circuit further comprises a second switch bias buffer circuit, comprising:
   a second voltage buffer configured to receive the sensing signal and to provide a second buffer signal at a second reduced impedance node, and
   a second switching circuit configured to modulate the output voltage of the second voltage buffer, the second switch bias buffer circuit being configured to operate in reverse with respect to the first switch bias buffer circuit.

2. The hearing aid according to claim 1, wherein the first MOSFET transistor is a common-drain MOSFET transistor, the first terminal being the source terminal of the common-drain MOSFET transistor.

3. The hearing aid according to claim 1, wherein the second voltage buffer comprises a second MOSFET transistor having a first terminal, a second terminal and a third terminal,
   the second switching circuit being configured to switch the voltage at the first terminal of said second MOSFET transistor:
   to the voltage at the output of the second switch bias buffer circuit when the first switching circuit switches the voltage at the first terminal of the first MOSFET transistor to the reference voltage, and
   to the reference voltage when the first switching circuit switches the voltage at the first terminal of the first MOSFET transistor to the voltage at the output of the first switch bias buffer circuit.

4. The hearing aid according to claim 1, wherein the at least one sensing signal processing circuit further comprises a first bias circuit, the first bias circuit being configured to reduce the flicker noise at the first terminal of the first MOSFET transistor, the first bias circuit comprising:
   a first current mirror, comprising two transistors, and
   a first bias switch configured the switch the voltages at the gate terminals of the two transistors of the first current mirror between a bias node voltage and a supply voltage.

5. The hearing aid according to claim 1, wherein the at least one sensing signal processing circuit further comprises a second bias circuit, the second bias circuit being configured to reduce the flicker noise at the first terminal of the second MOSFET transistor, the second bias circuit comprising:
   a second current mirror, comprising two transistors, and
   a second bias switch configured to switch the voltages at the gate terminals of the two transistors of the second current mirror between the bias node voltage and the supply voltage, in a reverse manner with respect to the first bias switch.

6. The hearing aid according to claim 1, wherein the at least one sensing signal processing circuit further comprises a chopper amplifier, configured to:
   modulate the frequency of the output signal of the at least one sensing signal processing circuit,
   amplify the modulated output signal, and
   demodulate the frequency of the amplified signal.

7. A hearing aid according to claim 1, wherein the hearing aid is configured to compensate a hearing loss of a user of the hearing aid, comprising:
   a microphone configured to receive an acoustic wave and provide an audio signal based on the acoustic wave,
   a signal processor unit configured to process the audio signal and provide a processed audio signal, and
   an output transducer configured to output the processed audio signal to the user,
   and wherein the signal processor unit is configured to process the audio signal based on the output signal of the at least one sensing signal processing circuit or is configured to adapt a hearing profile stored within a memory of the hearing aid based on the output signal of the at least one sensing signal processing circuit.

8. A hearing aid according to claim 1, comprising:
an in-the-ear unit,
a behind-the-ear unit,
a communication link configured to provide an electrical connection between the in-the-ear unit and the behind-the-ear unit,
a processor unit configured to receive the output signal of the at least one sensing signal processing circuit via the communication link,
wherein the at least one sensor is arranged in the in-the-ear unit, and the processor unit is arranged in the behind-the-ear unit of the hearing aid.

9. A hearing aid according to claim 8, wherein the communication link is a communication bus or a wireless communication link.

10. A hearing aid according to claim 1, comprising a housing that includes the at least one sensor and the at least one sensing signal processing circuit.

11. A hearing aid according to claim 1, wherein the at least one sensor is a capacitive sensor configured to provide a capacitive sensing signal.

12. A hearing aid according to claim 1, wherein the at least one sensor is an electrode configured to provide an EEG signal.

* * * * *